US012597504B2

(12) United States Patent
Yu et al.

(10) Patent No.: US 12,597,504 B2
(45) Date of Patent: Apr. 7, 2026

(54) AUTOMATIC SELECTION AND DISPLAY LAYOUT OF MEDICAL IMAGES FROM CLINICAL DESCRIPTIONS

(71) Applicant: Siemens Healthineers AG, Forchheim (DE)

(72) Inventors: Daphne Yu, Yardley, PA (US); Yamini Varadan, East Brunswick, NJ (US); Poikavila Ullaskrishnan, Lebanon, NH (US)

(73) Assignee: Siemens Healthineers AG, Forchheim (DE)

( * ) Notice: Subject to any disclaimer, the term of this patent is extended or adjusted under 35 U.S.C. 154(b) by 179 days.

(21) Appl. No.: 18/512,315

(22) Filed: Nov. 17, 2023

(65) Prior Publication Data

US 2025/0166791 A1    May 22, 2025

(51) Int. Cl.
| | |
|---|---|
| *G16H 30/20* | (2018.01) |
| *G06F 3/0484* | (2022.01) |
| *G06V 10/40* | (2022.01) |
| *G06V 10/75* | (2022.01) |
| *G06V 10/94* | (2022.01) |
| *G10L 15/18* | (2013.01) |

(52) U.S. Cl.
CPC ........... *G16H 30/20* (2018.01); *G06F 3/0484* (2013.01); *G06V 10/40* (2022.01); *G06V 10/75* (2022.01); *G06V 10/945* (2022.01); *G10L 15/1822* (2013.01); *G06V 2201/03* (2022.01)

(58) Field of Classification Search
CPC ........ G16H 30/20; G06V 10/40; G06V 10/75; G06V 10/945; G06V 2201/03; G06F 3/048; G10L 15/1822
See application file for complete search history.

(56) References Cited

U.S. PATENT DOCUMENTS

| | | | | |
|---|---|---|---|---|
| 8,923,580 | B2 | 12/2014 | Dekel et al. | |
| 9,152,760 | B2 | 10/2015 | Sherman et al. | |
| 9,575,994 | B2 * | 2/2017 | Kramer | .................. G06F 16/583 |
| 9,922,268 | B2 * | 3/2018 | Iwamura | ................ G16H 15/00 |
| 12,004,901 | B2 * | 6/2024 | Ulman | ................. A61B 8/0866 |

(Continued)

FOREIGN PATENT DOCUMENTS

| | | | |
|---|---|---|---|
| DE | 102012200076 A1 | 7/2013 | |
| WO | WO-2022033937 A1 * | 2/2022 | ............. G16H 30/20 |

OTHER PUBLICATIONS

Puentes et al., Enhancing Electronic Patient Record Functionality through Information Extraction from Images, 2006, IEEE, 6 pages. (Year: 2006).*

(Continued)

*Primary Examiner* — Linh K Pham

(57) ABSTRACT

Systems and methods for automatic selection and display layout of medical images are provided. User input comprising 1) a description of desired medical images and 2) viewing preferences for the desired medical images is received. One or more nodes of a clinical knowledge ontological database that match the description of the desired medical images are determined. The one or more matching nodes are associated with one or more medical images in the clinical knowledge ontological database. A display layout of the one or more medical images is generated based on the viewing preferences. The display layout is output.

20 Claims, 8 Drawing Sheets

<u>400</u>

(56) References Cited

U.S. PATENT DOCUMENTS

| | | | | |
|---|---|---|---|---|
| 12,068,067 | B2* | 8/2024 | Budz | G06T 7/0014 |
| 2005/0022114 | A1* | 1/2005 | Shanahan | G06F 21/10 |
| | | | | 715/234 |
| 2007/0160275 | A1* | 7/2007 | Sathyanarayana | G16H 10/60 |
| | | | | 382/128 |
| 2010/0131514 | A1* | 5/2010 | Pan | G16H 70/60 |
| | | | | 707/E17.014 |
| 2010/0293164 | A1* | 11/2010 | Weese | G06F 16/5866 |
| | | | | 707/E17.014 |
| 2012/0027273 | A1* | 2/2012 | Zankowski | G06T 7/33 |
| | | | | 382/128 |
| 2012/0066241 | A1* | 3/2012 | Geller | G16H 30/20 |
| | | | | 707/E17.02 |
| 2012/0166219 | A1* | 6/2012 | Mansour | G16H 10/60 |
| | | | | 705/3 |
| 2015/0161786 | A1* | 6/2015 | Seifert | A61B 6/5211 |
| | | | | 382/119 |
| 2015/0347464 | A1* | 12/2015 | Takata | G16H 50/00 |
| | | | | 707/728 |
| 2016/0267222 | A1* | 9/2016 | Larcom | G16H 30/20 |
| 2019/0057503 | A1* | 2/2019 | Nakamura | G06T 7/0014 |
| 2020/0019617 | A1* | 1/2020 | Eswaran | G06T 7/0016 |
| 2021/0019342 | A1* | 1/2021 | Peng | G06F 16/583 |
| 2021/0158933 | A1* | 5/2021 | Frosch | G16H 30/40 |
| 2021/0183070 | A1* | 6/2021 | Laaksonen | G06T 7/149 |
| 2021/0248716 | A1* | 8/2021 | Vera-Gonzalez | G16H 30/20 |
| 2021/0267570 | A1* | 9/2021 | Ulman | G06T 5/40 |
| 2021/0358600 | A1* | 11/2021 | Yerebakan | G06F 16/5866 |
| 2022/0122256 | A1* | 4/2022 | Hartkens | G16H 50/20 |
| 2022/0122717 | A1* | 4/2022 | Budz | G16H 30/40 |
| 2022/0405336 | A1* | 12/2022 | Lippe | G06F 16/9535 |
| 2023/0111306 | A1* | 4/2023 | Anand | G06T 7/0014 |
| | | | | 382/128 |
| 2023/0154593 | A1* | 5/2023 | Gao | G16H 30/40 |
| | | | | 382/181 |
| 2023/0253117 | A1* | 8/2023 | Singh | G16H 30/40 |
| | | | | 705/2 |
| 2023/0368878 | A1* | 11/2023 | Molenda | G16H 70/60 |
| 2024/0153072 | A1* | 5/2024 | Mackinnon | G06T 7/0012 |

OTHER PUBLICATIONS

Putra et al., Portable Device-Based Medical Service System For DICOM To PNG Conversion, 2021, IEEE, 7 pages (Year: 2021).*

Enhancing Electronic Patient Record Functionality Through Information Extraction from Images (Year: 2006).*

Portable Device-Based Medical Service System For DICOM To PNG Conversion (Year: 2021).*

Kapoor et al., Infrastructure tools to support an effective Radiation Oncology Learning Health System, Aug. 25, 2023, PubMed Center, 19 pages. (Year: 2023).*

Walke et al., The importance of graph databases and graph learning for clinical applications, 2024, PubMed Center, 20 pages. ( Year: 2024).*

\* cited by examiner

Figure 1:
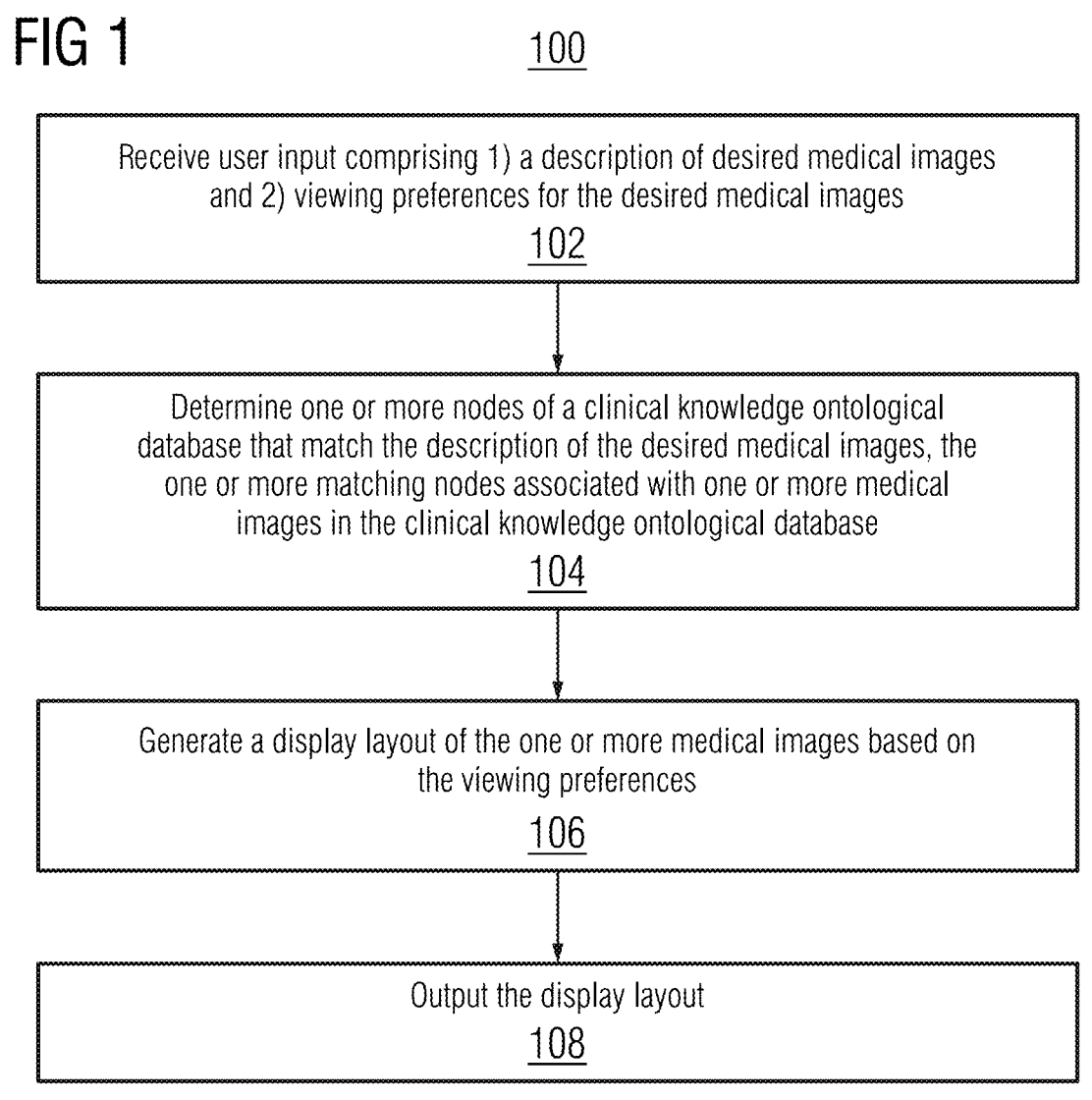

FIG 1                                    100

Receive user input comprising 1) a description of desired medical images
and 2) viewing preferences for the desired medical images
102

Determine one or more nodes of a clinical knowledge ontological
database that match the description of the desired medical images, the
one or more matching nodes associated with one or more medical
images in the clinical knowledge ontological database
104

Generate a display layout of the one or more medical images based on
the viewing preferences
106

Output the display layout
108

FIG 3                                  300

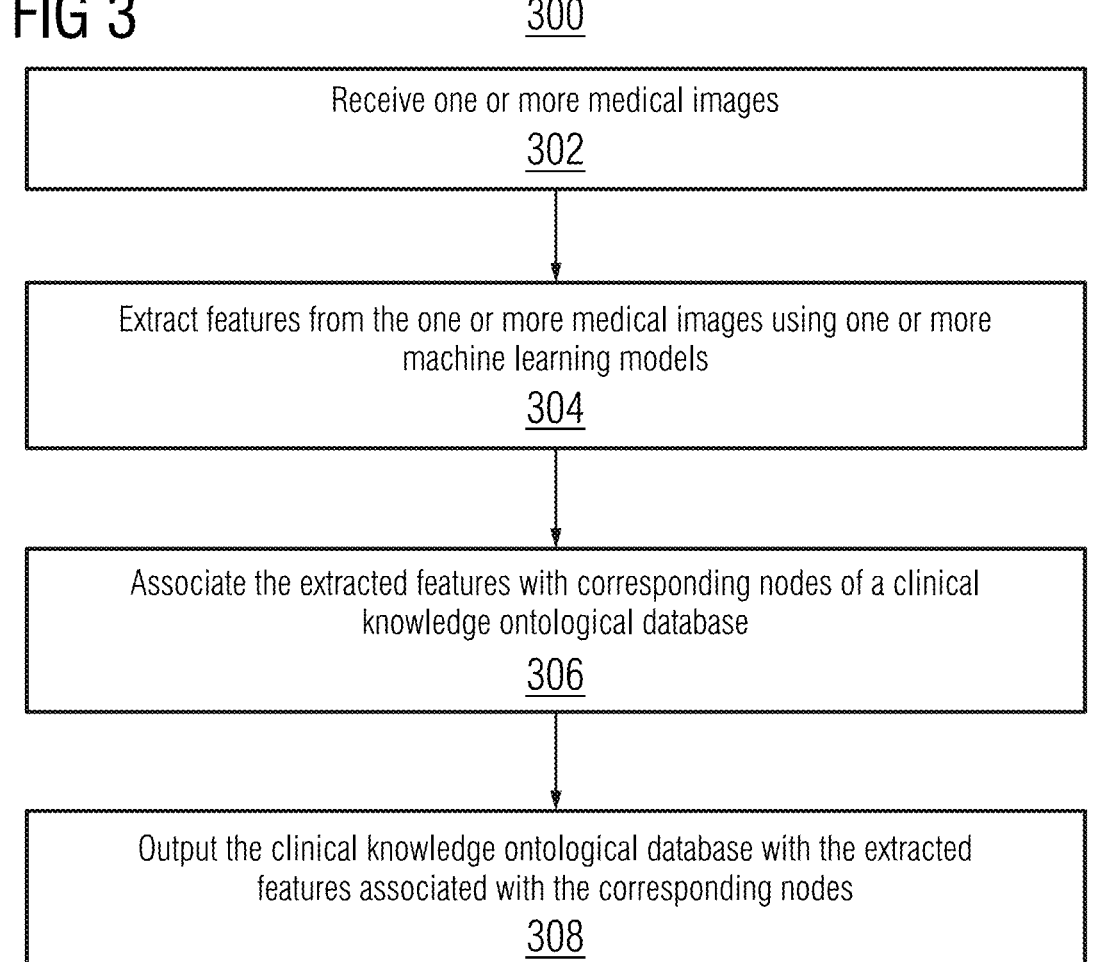

Receive one or more medical images
302

Extract features from the one or more medical images using one or more
machine learning models
304

Associate the extracted features with corresponding nodes of a clinical
knowledge ontological database
306

Output the clinical knowledge ontological database with the extracted
features associated with the corresponding nodes
308

AUTOMATIC SELECTION AND DISPLAY LAYOUT OF MEDICAL IMAGES FROM CLINICAL DESCRIPTIONS

TECHNICAL FIELD

The present invention relates generally to automatic selection and display layout of medical images, and in particular to automatic selection and display layout of medical images from clinical descriptions.

BACKGROUND

In radiology, medical images of a patient are acquired for clinical analysis by radiologists. To facilitate efficient reading of such medical images, radiologists typically prefer consistent and optimal display layout of such medical images. Currently, the display layout of medical images is defined by configuring data properties and view settings, which requires specialized technical knowledge of specific vendor software implementation. However, clinicians typically communicate in clinical nomenclature and do not possess the technical knowledge required for configuring the display layout of medical images.

BRIEF SUMMARY OF THE INVENTION

In accordance with one or more embodiments, systems and methods for automatic selection and display layout of medical images are provided. User input comprising 1) a description of desired medical images and 2) viewing preferences for the desired medical images is received. One or more nodes of a clinical knowledge ontological database that match the description of the desired medical images are determined. The one or more matching nodes are associated with one or more medical images in the clinical knowledge ontological database. A display layout of the one or more medical images is generated based on the viewing preferences. The display layout is output.

In one embodiment, the user input further comprises a temporal description of the desired medical images. The one or more nodes of the clinical knowledge ontological database that match the description of the desired medical images are determined based on the temporal description of the desired medical images.

In one embodiment, the user input is parsed into vectors. A vector search between the vector representing the description of the desired medical images and vectors representing nodes of the clinical knowledge ontological database is performed to identify a list of ranked nodes. One or more highest ranking nodes that satisfy a ranking threshold are identified as the one or more nodes.

In one embodiment, the clinical knowledge ontological database is generated by receiving one or more medical images, extracting features from the one or more medical images using one or more machine learning models, associating the extracted features with corresponding nodes of the clinical knowledge ontological database, and outputting the clinical knowledge ontological database with the extracted features associated with the corresponding nodes.

In one embodiment, the description of desired medical images comprises a description of an anatomical object of interest to which to navigate within one or more medical images and the one or more matching nodes comprise one or more matching nodes associated with coordinates of the anatomical object of interest in the one or more medical images.

In one embodiment, the description of the desired medical images is defined based on at least one of imaging modality, acquisition parameter, acquisition orientation, image appearance, anatomical field of view, or classifications and detections. In one embodiment, the viewing preferences are defined based on at least one of anatomical display orientation, windowing, or rendering mode.

In one embodiment, the viewing preferences are translated to rendering parameters using a language model.

In one embodiment, the display layout is displayed on a display device.

These and other advantages of the invention will be apparent to those of ordinary skill in the art by reference to the following detailed description and the accompanying drawings.

BRIEF DESCRIPTION OF THE DRAWINGS

FIG. 1 shows a method for automatically generating a display layout of one or more medical images, in accordance with one or more embodiments;

FIG. 3 shows a method for generating a clinical knowledge ontological database, in accordance with one or more embodiments;

DETAILED DESCRIPTION

Figure 2:
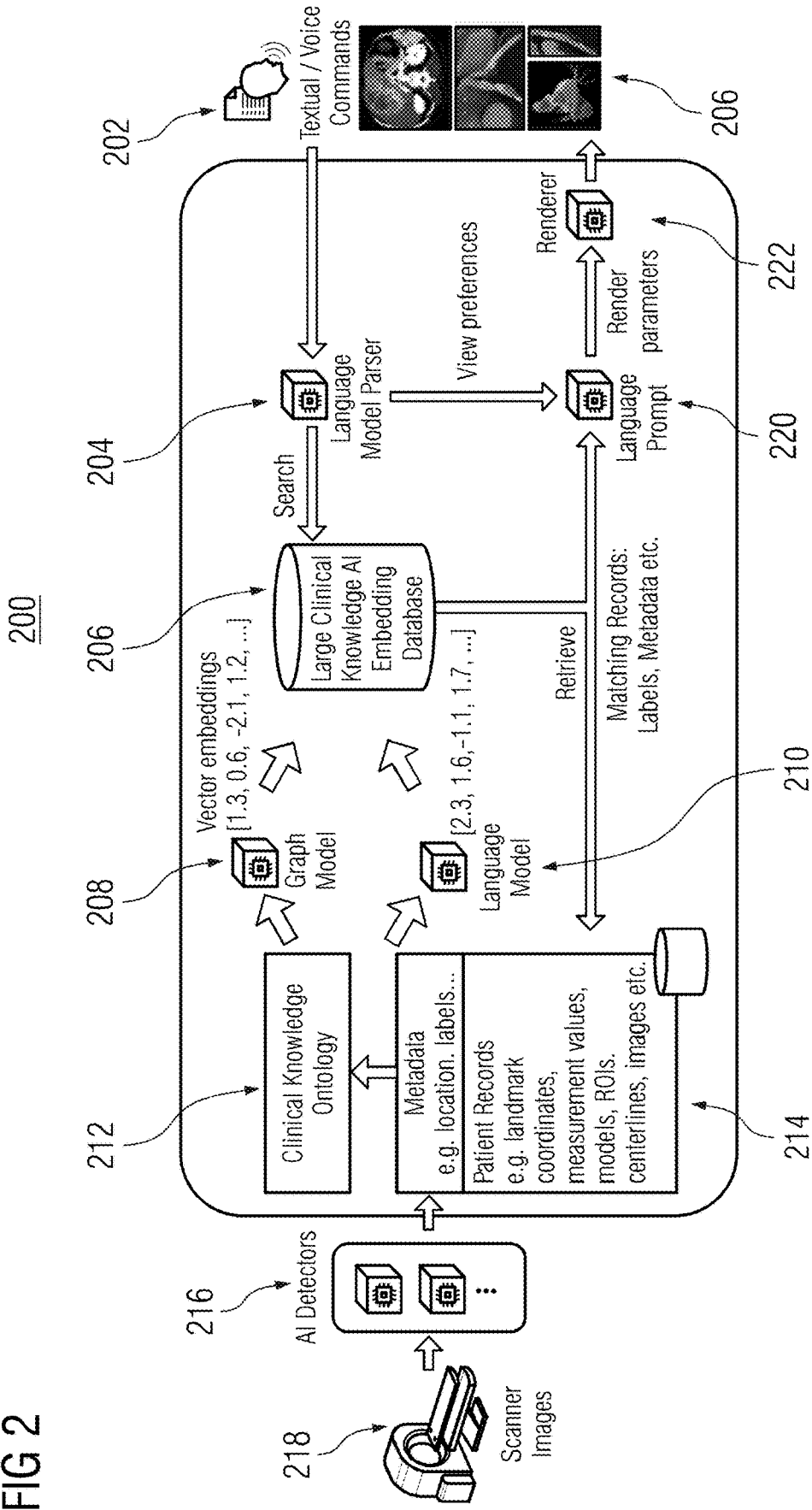
FIG. 2 shows a workflow for automatically generating a display layout of one or more medical images, in accordance with one or more embodiments.

The present invention generally relates to methods and systems for automatic selection and display layout of medical images from clinical descriptions. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa. Embodiments of the present invention are described with references to the figures, where like reference numerals refer to the same or similar elements.

Embodiments described herein provide for a display layout system for automatic selection and display layout of medical images from arbitrary, natural language clinical phrases received as user input from a user (e.g., radiologist). The user input comprises a description of desired medical images and viewing preferences for the desired medical images. The description of the desired medical images is matched with one or more nodes of a clinical knowledge ontological database of clinical nomenclature, where the one or more nodes are associated with one or more medical images a priori. A display layout of the one or more medical images is automatically generated based on the viewing preferences. Advantageously, the display layout system provides a robust translation of user input of instructions in clinical nomenclature to closely related medical images. The use of a language model also enables the translation of partially described viewing preferences to internal viewing implementations.

FIG. 1 shows a method 100 for automatically generating a display layout of one or more medical images, in accordance with one or more embodiments. The steps and substeps of method 100 may be performed by one or more suitable computing devices, such as, e.g., computer 802 of FIG. 8. FIG. 2 shows a workflow 200 for automatically generating a display layout of one or more medical images, in accordance with one or more embodiments. FIG. 1 and FIG. 2 will be described together.

At step 102 of FIG. 1, user input comprising 1) a description of desired medical images and 2) viewing preferences for the desired medical images is received. The user input may be received from a radiologist, a clinician, or any other user. The user input may be defined in clinical nomenclature in an arbitrary, unstructured format. The user input may be received as text, voice, or in any other suitable form. One example of the user input is: "T2 with a date one before the most recent, display with lung window in the anterior orientation." In one example, as shown in workflow 200 of FIG. 2, the user input is textual/voice commands 202.

The description of the desired medical images may be defined, for example, based on at least one of imaging modality, acquisition parameter, acquisition orientation, image appearance, anatomical field of view, classifications and detections (e.g., presence of anatomical objects of interest, such as, e.g., organs, vessels, bones, tumors, pathologies, etc.), and/or any other suitable description of the desired medical images. The viewing preferences for the desired medical images may be defined, for example, based on at least one of anatomical display orientation, windowing, rendering mode, and/or any other suitable viewing preferences.

In one embodiment, the user input received at step 102 of FIG. 2 further comprises a temporal description of the desired medical images, such as, for example, dates or a relative description of temporal order.

Figure 8:
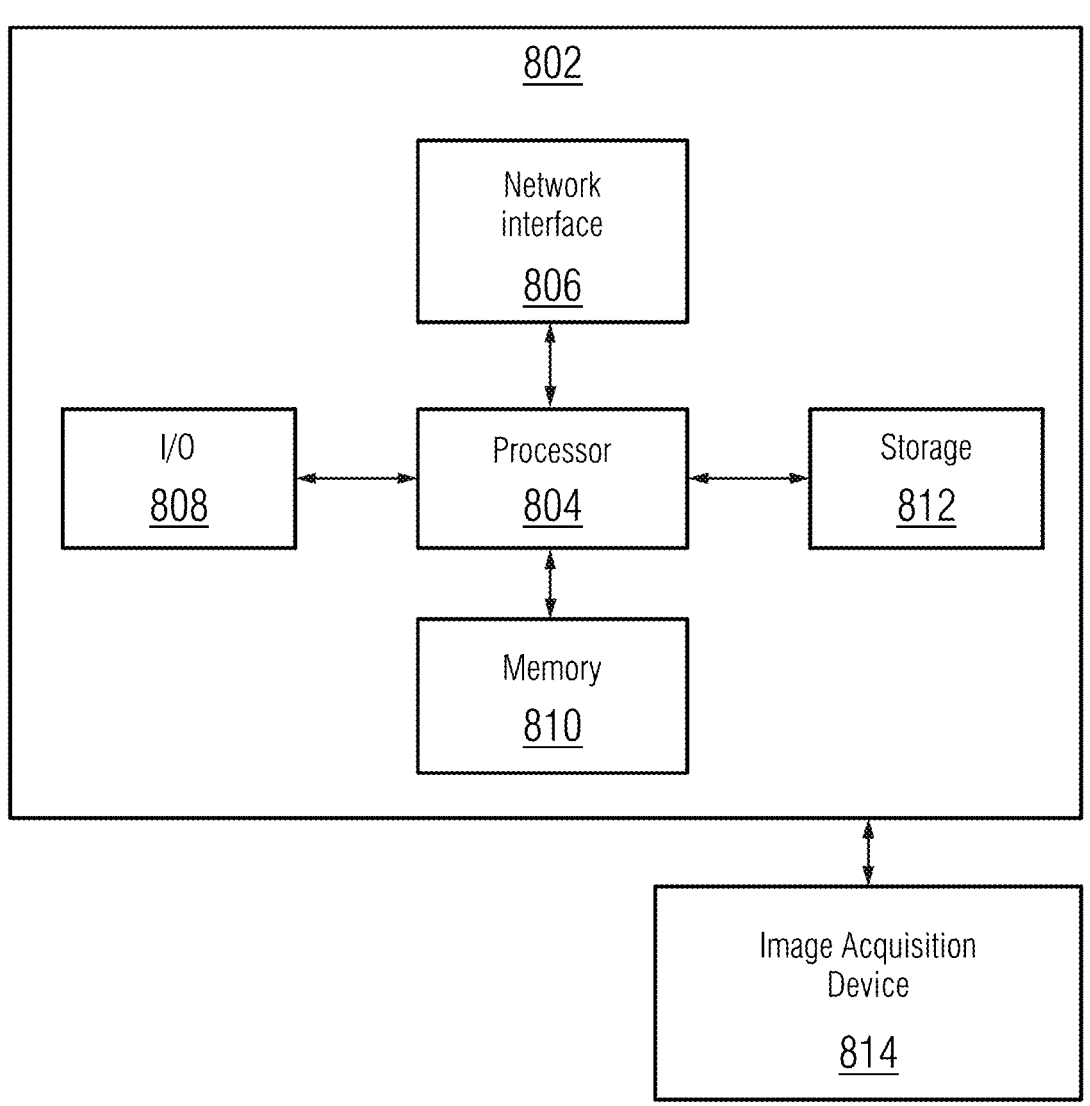
FIG. 8 shows a high-level block diagram of a computer that may be used to implement one or more embodiments.

The user input may be received, for example, from the user interacting with an I/O (input/output) device of a computer system (e.g., I/O device 808 of computer 802 of FIG. 8), by loading the user input from a storage or memory (e.g., memory 810 or storage 812 of computer 802 of FIG. 8) of a computer system, or by receiving the user input from a remote computer system (e.g., computer 802 of FIG. 8).

At step 104 of FIG. 1, one or more nodes of a clinical knowledge ontological database that match the description of the desired medical images are determined. The one or more matching nodes are associated with one or more medical images in the clinical knowledge ontological database. In one example, as shown in workflow 200 of FIG. 2, the clinical knowledge ontological database is large clinical knowledge AI (artificial intelligence) embedding database 206 and the one or more nodes in large clinical knowledge AI embedding database 206 that match the description of desired medical images are determined.

To determine the one or more nodes that match the description of the desired medical images, as shown in workflow 200 of FIG. 2, the user input textual/voice commands 202 are first interpreted by language model parser 204 to extract 1) the description of the desired medical images, 2) the viewing preferences, and 3) (optionally) the temporal description of the desired medical images as respective vector representations. Language model parser 204 may be implemented according to any suitable (e.g., well-known) approach. The vector representation of the description of the desired medical images extracted from textual/voice commands 202 is then input into the large clinical knowledge AI embedding database 206 to search for the one or more nodes having a vector representation that match the vector representation of the description of the desired medical images. The search may be performed using any suitable vector similarity algorithm, such as, e.g., cosine similarity. The results of the vector search are a list of ranked nodes within large clinical knowledge AI embedding database 206 that are similar to the description of the desired medical images. The highest matching node (or the top N nodes, where N is any positive integer) that also satisfies a ranking threshold is selected as the one or more matching nodes and the one or more medical images associated with the one or more matching nodes are identified.

Optionally, in one embodiment, where the temporal description of the desired medical images is received at step 102 of FIG. 1, the search may be further constrained to the nodes in large clinical knowledge AI embedding database 206 that satisfy the temporal description (e.g., date range). In one embodiment, the search may be constrained according to the temporal description by prompting language model 210 for a list of available image acquisition dates and asking language model 210 to identify the nodes that satisfy the temporal description. The vector search may then be performed on the identified nodes that satisfy the temporal description.

Language model 210 may be any suitable language model. In one embodiment, language model 210 may be a machine learning based language model. For example, in one embodiment, language model 210 may be a custom, relatively smaller language model for natural language processing, such as, e.g., BERT (Bidirectional Encoder Representations from Transformers). In another embodiment, language model 210 may be a pre-trained deep learning based LLM (large language model). For example, the LLM may be based on the transformer architecture, which uses a self-attention mechanism to capture long-range dependencies in text. One example of a transformer-based architecture is GPT (generative pre-training transformer), which has a multilayer transformer decoder architecture that may be pretrained to optimize the next token prediction task and then fine-tuned with labelled data for various downstream tasks. GPT-based LLMs may be trained using reinforcement learning with human feedback for performing various natural language processing tasks.

Large clinical knowledge AI embedding database 206 is generated a priori to model clinical nomenclature of medical images as a graph comprising plurality of nodes connected by edges. Each node is represented as a vector representation associated with clinical nomenclature of medical images. Large clinical knowledge AI embedding database 206 may be generated according to FIG. 3, described in detail below.

At step 106 of FIG. 1, a display layout of the one or more medical images is generated based on the viewing preferences. In one example, as shown in workflow 200 of FIG. 2, the viewing preferences extracted from textual/voice commands 202 by language model parser 204 are sent to language prompt 220 to translate the viewing preferences to rendering parameters and renderer 222 generates display layout 224 according to the rendering parameters. Language prompt 220 is a prompt or input to language model 210 defining the specific rendering input schema. For example, language prompt 220 may indicate to language model 210 that renderer 222 can support viewing the patient in the anterior, left, and right orientations and instruct language model 210 to translate the user input viewing preferences to one of these orientations. Other viewing preferences (e.g., windowing presets, available render modes, etc.) can be similarly translated.

At step 108 of FIG. 1, the display layout is output. For example, the display layout can be output by displaying the display layout on a display device (e.g., I/O device 808 of computer 802 of FIG. 8) of a computer system, by storing display layout on a memory or storage (e.g., memory 810 or storage 812 of computer 802 of FIG. 8) of a computer system, or by transmitting the display layout to a remote computer system (e.g., computer 802 of FIG. 8).

Embodiments described herein may be implemented in, e.g., PACS (picture archiving and communication system) viewer applications. For example, when a user loads a patient in a PACS viewer application, the user can provide user input in a chat window and the system may automatically select medical images and generate the display layout for displaying the medical images to the user.

FIG. 3 shows a method 300 for generating a clinical knowledge ontological database, in accordance with one or more embodiments. The steps or sub-steps of method 300 may be performed by one or more suitable computing devices, such as, e.g., computer 802 of FIG. 8. Method 300 of FIG. 3 will be described with continued reference to workflow 200 of FIG. 2. In one example, method 300 of FIG. 3 is performed a priori to step 104 of FIG. 1 to generate the clinical knowledge ontological database utilized at step 104 of FIG. 1.

At step 302 of FIG. 3, one or more medical images are received. In one example, as shown in workflow 200 of FIG. 2, the one or more medical images are scanner images 218. The one or more medical images may depict any anatomical object of interest, such as, e.g., organs, bones, vessels, abnormalities, etc. The one or more medical images may be of any suitable modality, such as, e.g., CT (computed tomography), MRI (magnetic resonance imaging), US (ultrasound), x-ray, or any other medical imaging modality or combinations of medical imaging modalities. The one or more medical images may be 2D (two dimensional) images, 3D (three dimensional) volumes, or 4D (four dimensional) volumes (3D plus time). The one or more medical images may be received, for example, directly from an image acquisition device (e.g., image acquisition device 814 of FIG. 8) as the medical images are acquired, by loading previously acquired medical images from a storage or memory (e.g., memory 810 or storage 812 of computer 802 of FIG. 8) of a computer system, or by receiving medical images from a remote computer system (e.g., computer 802 of FIG. 8).

At step 304 of FIG. 3, features are extracted from the one or more medical images using one or more machine learning models. In one example, as shown in workflow 200 of FIG. 2, features 214 are extracted from scanner images 218 using AI detectors 216. The features may comprise, for example, metadata of the images (e.g., acquisition type, location, labels), patient records (e.g., landmark coordinates, measurement values, models, ROIs (regions of interest) centerlines, images, anatomical field of view, presence of pathologies such as, e.g., lesions or foreign objects, etc.), or any other suitable features extracted from the one or more medical images. The one or more machine learning models converts imaging data of the one or more medical images into text-based labels and metadata. The one of more machine learning models may be implemented using any suitable (e.g., well-known) technique for performing medical imaging analysis tasks.

At step 306 of FIG. 3, the extracted features as associated with corresponding nodes of a clinical knowledge ontological database. In one example, as shown in workflow 200 of FIG. 2, the clinical knowledge ontological database is large clinical knowledge AI embedding database 206 and features 214 are mapped to nodes of clinical knowledge ontology 212 using graph model 208 and language model 210 to generate large clinical knowledge AI embedding database 206. The clinical knowledge ontological database is created to include all nodes within an ontological database modeling clinical nomenclature. The nodes are represented as language embedded vectors of the descriptions and aliases. The clinical knowledge ontological database may be based on standard ontology graphs, such as, e.g., RadLex, UMLS (unified medical language system), or any other suitable imaging ontology. Optionally, a graph model 208 may be created to store relationships between nodes and edges to allow for more indirect description associations. For generating embeddings or vector representation of features 214, embedding models (e.g., text-ada-embedding-002 or even fine-tuned BERT) are used. In language model 210, features and DICOM (digital imaging and communications in medicine) tags of the image (e.g., modality, study date, view position, pixel array, study description) and their link to the ontology concepts (e.g., RadLex identifiers) are converted to a paragraph description and stored as embeddings. In graph model 208, the links between ontology concepts are stored as embeddings (e.g., MR concept is a child of Diagnostic Imaging). These two types of embeddings are then combined to find a closest matching one to the user request. Graph model 208 is utilized since, if the request was for abstract diagnostic imaging, it will still find MR images.

In one embodiment, the extracted features are associated with the corresponding nodes based further on image metadata, which may be non-standardized and potentially vendor specific. For example, the extracted features may comprise image acquisition using contrast with an MR (magnetic resonance) protocol. The image acquisition label and the associated MR acquisition parameters are then associated with the corresponding node for subsequent retrieval.

At step 308 of FIG. 3, the clinical knowledge ontological database with the extracted features associated with the corresponding nodes is output. For example, the clinical knowledge ontological database can be output by storing the clinical knowledge ontological database on a memory or storage (e.g., memory 810 or storage 812 of computer 802 of FIG. 8) of a computer system or by transmitting the clinical knowledge ontological database to a remote computer system (e.g., computer 802 of FIG. 8).

Figure 4:
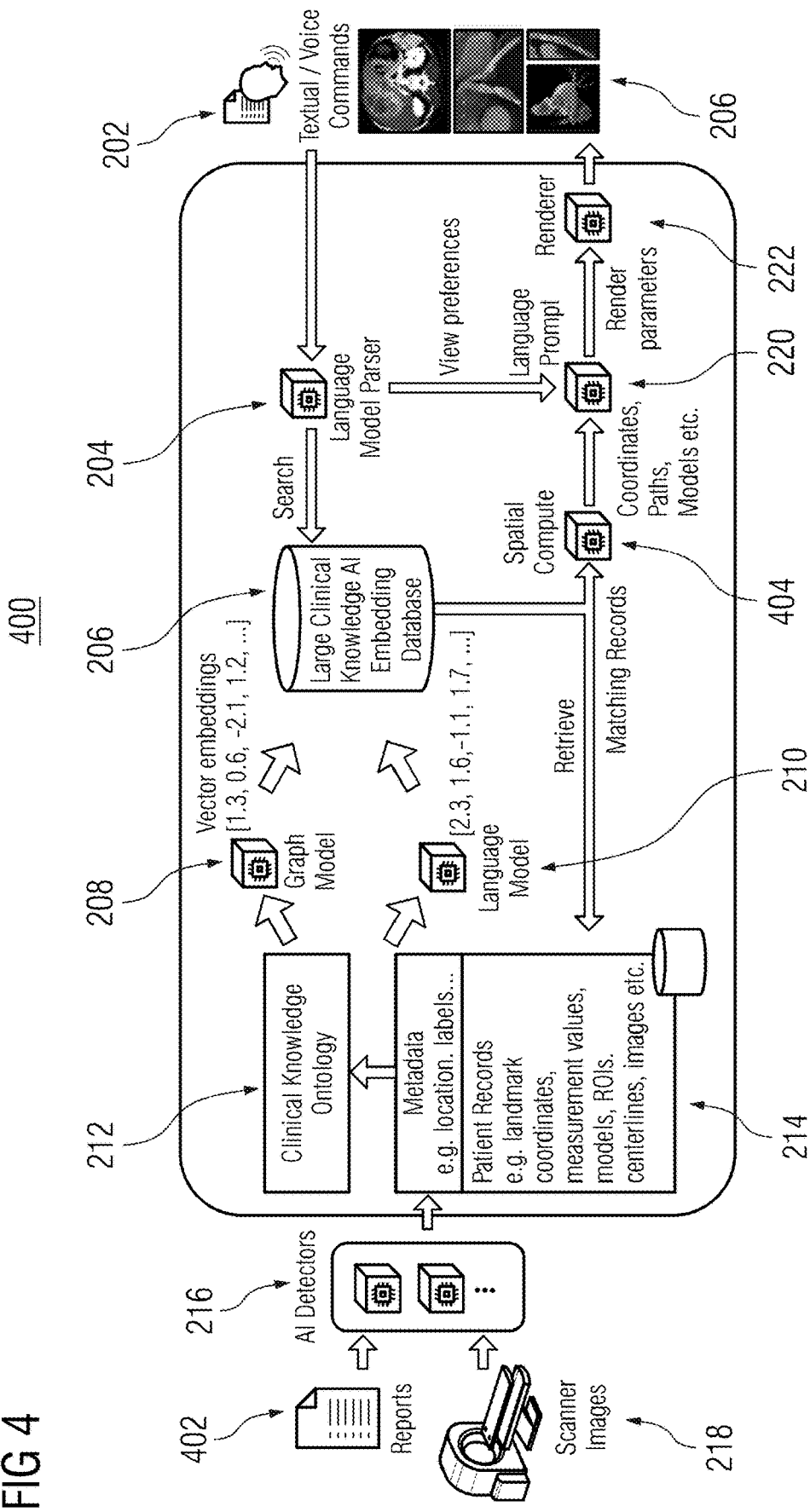
FIG. 4 shows a workflow for automatic medical image navigation, in accordance with one or more embodiments.

In one embodiment, method 100 of FIG. 1 may be applied for automatically navigating within a medical image to a specific anatomical location based on user input. FIG. 4 shows a workflow 400 for automatic medical image navigation, in accordance with one or more embodiments. Workflow 400 of FIG. 4 is an extension of workflow 200 of FIG. 2 to enable automatic medical image navigation. Workflow 400 of FIG. 4 will be described with reference to method 100 of FIG. 1.

To generate large clinical knowledge AI embedding database 206, for example during an a prior pre-processing stage, AI detectors 216 are applied for detecting features 214 from scanner images 218. Features 214 comprise spatial features representing anatomical textual labels associated with, e.g., detected spatial coordinates, region of interest masks, models, etc. of an anatomical object of interest (e.g., organs, bones, vessels, tumors, etc.). The anatomical textual labels are concepts expressed in high degree of detail within large clinical knowledge AI embedding database 206 as interconnected graphs of nodes. Each of the detected anatomical labels is associated with one or more corresponding nodes. The detected spatial features 214 are then stored in a patient record database associated with the nodes. Similarly, text features 214 may be extracted from text-based reports 402 are detected using AI detectors 216. Such text features 214 may comprise phrases in reports 402, such as, e.g., phrases describing anatomical regions where anomalies are described, phrases describing pathologies that occur at specific anatomical structures, etc. The extracted text features 214 are associated with corresponding nodes in large clinical knowledge AI embedding database 206. Since pathologies and locations where such pathologies occur are connected within the ontology graph, the association between pathology and location are established. Based on the a priori generated large clinical knowledge AI embedding database 206 of spatial feature relationships, method 100 may be performed for automatic medical image navigation.

At step 102 of FIG. 1, user input comprising 1) a description of desired medical images and 2) viewing preferences for the desired medical images is received. The description of desired medical images comprises a description of an anatomical object of interest to which to navigate within one or more medical images. Examples of the user input are: "go to lungs in nodules are detected, otherwise start at the pancreatic head using an abdominal window" or "go to the hepatic hypodensity at segment IV."

At step 104 of FIG. 1, one or more nodes of a clinical knowledge ontological database that match the description of the desired medical images are determined. Within the patient image coordinate nodes, the highest ranking matching nodes are determined that are associated with medical images that have detected anatomical objects of interest that match the description of the desired medical images. If a match is found, the associated coordinates are used to navigate to that location in the associated medical images. In one example, as shown in workflow 400 of FIG. 4, spatial compute 404 computes the spatial information (e.g., coordinates, paths, models, etc.) for navigation. In one embodiment, a post-processing step may be performed to convert 3D coordinates to a specific view. For example, a post-processing step may be performed to generate a reformatting, clip plane, or surface view from a plurality of coordinates. In another example, the coordinates may be used to further sample nearby pixels to optimize the windowing or transfer function to view that region.

At step 106 of FIG. 1, a display layout of the one or more medical images is generated based on the viewing preferences and at step 108 of FIG. 1 the display layout is output.

Embodiments described herein are described with respect to the claimed systems as well as with respect to the claimed methods. Features, advantages or alternative embodiments herein can be assigned to the other claimed objects and vice versa. In other words, claims and embodiments for the systems can be improved with features described or claimed in the context of the respective methods. In this case, the functional features of the method are implemented by physical units of the system.

Furthermore, certain embodiments described herein are described with respect to methods and systems utilizing trained machine learning models, as well as with respect to methods and systems for providing trained machine learning models. Features, advantages or alternative embodiments herein can be assigned to the other claimed objects and vice versa. In other words, claims and embodiments for providing trained machine learning models can be improved with features described or claimed in the context of utilizing trained machine learning models, and vice versa. In particular, datasets used in the methods and systems for utilizing trained machine learning models can have the same properties and features as the corresponding datasets used in the methods and systems for providing trained machine learning models, and the trained machine learning models provided by the respective methods and systems can be used in the methods and systems for utilizing the trained machine learning models.

In general, a trained machine learning model mimics cognitive functions that humans associate with other human minds. In particular, by training based on training data the machine learning model is able to adapt to new circumstances and to detect and extrapolate patterns. Another term for "trained machine learning model" is "trained function."

In general, parameters of a machine learning model can be adapted by means of training. In particular, supervised training, semi-supervised training, unsupervised training, reinforcement learning and/or active learning can be used. Furthermore, representation learning (an alternative term is "feature learning") can be used. In particular, the parameters of the machine learning models can be adapted iteratively by several steps of training. In particular, within the training a certain cost function can be minimized. In particular, within the training of a neural network the backpropagation algorithm can be used.

In particular, a machine learning model, such as, e.g., AI detectors 216 of FIG. 2, the one or more machine learning models utilized at step 304 of FIG. 3, or AI detectors 216 of FIG. 4, can comprise, for example, a neural network, a support vector machine, a decision tree and/or a Bayesian network, and/or the machine learning model can be based on, for example, k-means clustering, Q-learning, genetic algorithms and/or association rules. In particular, a neural network can be, e.g., a deep neural network, a convolutional neural network or a convolutional deep neural network. Furthermore, a neural network can be, e.g., an adversarial network, a deep adversarial network and/or a generative adversarial network.

Figure 5:
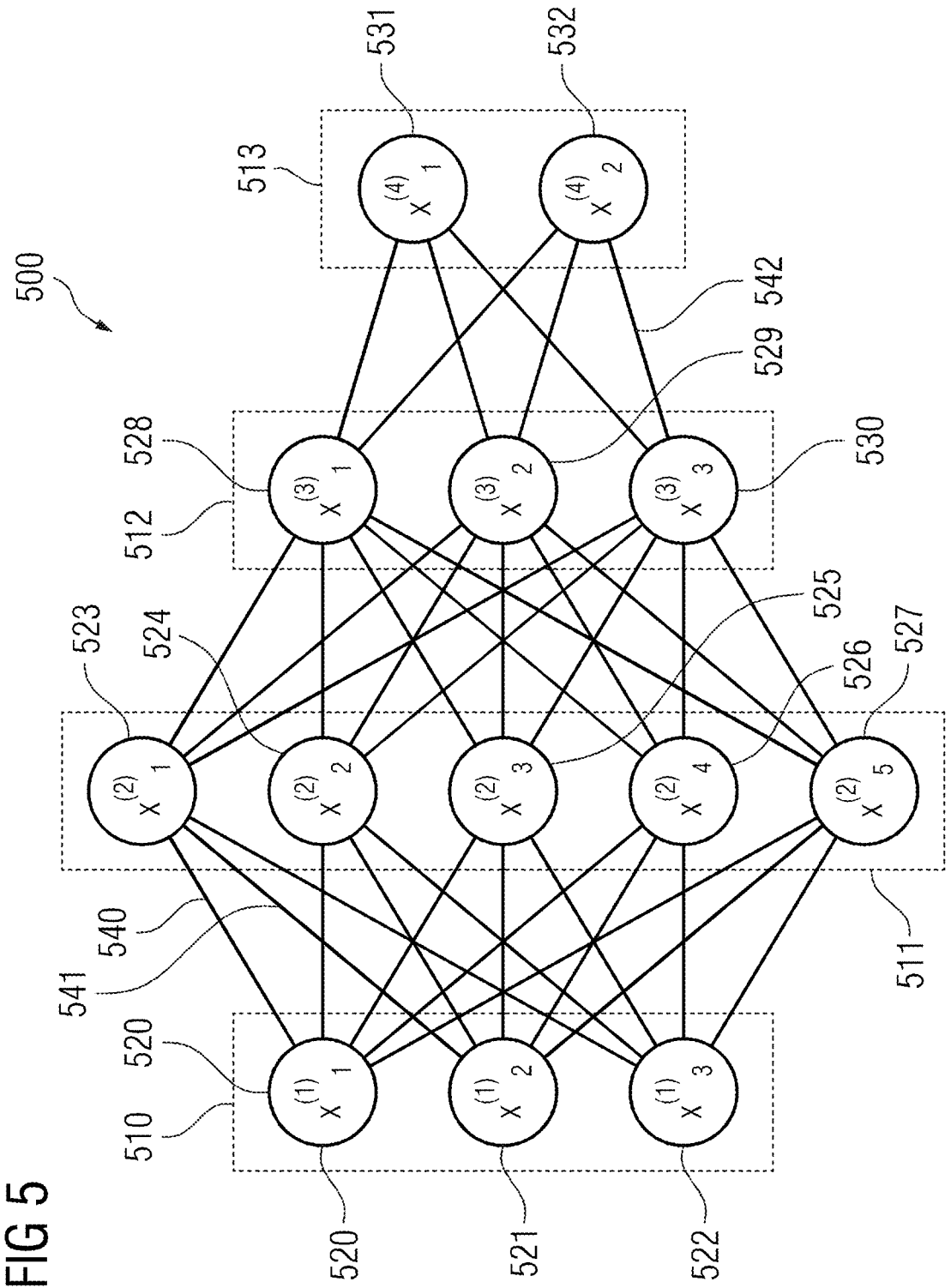
FIG. 5 shows an exemplary artificial neural network that may be used to implement one or more embodiments.

FIG. 5 shows an embodiment of an artificial neural network 500 that may be used to implement one or more machine learning models described herein. Alternative terms for "artificial neural network" are "neural network", "artificial neural net" or "neural net".

The artificial neural network 500 comprises nodes 520, . . . , 532 and edges 540, . . . 542, wherein each edge 540, . . . , 542 is a directed connection from a first node 520, . . . 532 to a second node 520, 532. In general, the first node 520, . . . , 532 and the second node 520, . . . , 532 are different nodes 520, . . . , 532, it is also possible that the first node 520, . . . , 532 and the second node 520, . . . , 532 are identical. For example, in FIG. 5 the edge 540 is a directed connection from the node 520 to the node 523, and the edge 542 is a directed connection from the node 530 to the node 532. An edge 540, . . . , 542 from a first node 520, . . . , 532 to a second node 520, . . . , 532 is also denoted as "ingoing edge" for the second node 520, . . . , 532 and as "outgoing edge" for the first node 520, . . . , 532.

In this embodiment, the nodes 520, . . . , 532 of the artificial neural network 500 can be arranged in layers 510, . . . , 513, wherein the layers can comprise an intrinsic order introduced by the edges 540, . . . , 542 between the nodes 520, . . . , 532. In particular, edges 540, . . . , 542 can exist only between neighboring layers of nodes. In the displayed embodiment, there is an input layer 510 comprising only nodes 520, . . . , 522 without an incoming edge, an output layer 513 comprising only nodes 531, 532 without outgoing edges, and hidden layers 511, 512 in-between the input layer 510 and the output layer 513. In general, the number of hidden layers 511, 512 can be chosen arbitrarily. The number of nodes 520, . . . , 522 within the input layer 510 usually relates to the number of input values of the neural network, and the number of nodes 531, 532 within the output layer 513 usually relates to the number of output values of the neural network.

In particular, a (real) number can be assigned as a value to every node 520, . . . 532 of the neural network 500. Here, $x^{(n)}_i$ denotes the value of the i-th node 520, . . . , 532 of the n-th layer 510, . . . , 513. The values of the nodes 520, . . . , 522 of the input layer 510 are equivalent to the input values of the neural network 500, the values of the nodes 531, 532 of the output layer 513 are equivalent to the output value of the neural network 500. Furthermore, each edge 540, . . . , 542 can comprise a weight being a real number, in particular, the weight is a real number within the interval $[-1, 1]$ or within the interval $[0, 1]$. Here, $w^{(m,n)}_{i,j}$ denotes the weight of the edge between the i-th node 520, . . . , 532 of the m-th layer 510, . . . , 513 and the j-th node 520, . . . , 532 of the n-th layer 510, . . . , 513. Furthermore, the abbreviation $w^{(n)}_{i,j}$ is defined for the weight $w^{(n,n+1)}_{i,j}$.

In particular, to calculate the output values of the neural network 500, the input values are propagated through the neural network. In particular, the values of the nodes 520, . . . , 532 of the (n+1)-th layer 510, . . . , 513 can be calculated based on the values of the nodes 520, . . . , 532 of the n-th layer 510, . . . , 513 by $$ x^{(n+1)}_j = f\left(\sum_i x^{(n)}_i \cdot w^{(n)}_{i,j}\right). $$

Herein, the function f is a transfer function (another term is "activation function"). Known transfer functions are step functions, sigmoid function (e.g., the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 510 are given by the input of the neural network 500, wherein values of the first hid-den layer 511 can be calculated based on the values of the input layer 510 of the neural network, wherein values of the second hidden layer 512 can be calculated based in the values of the first hidden layer 511, etc.

In order to set the values $w^{(m,n)}_{i,j}$ for the edges, the neural network 500 has to be trained using training data. In particular, training data comprises training input data and training output data (denoted as $t_i$). For a training step, the neural network 500 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 500 (backpropagation algorithm). In particular, the weights are changed according to $$ w'^{(n)}_{i,j} = w^{(n)}_{i,j} - \gamma \cdot \delta^{(n)}_j \cdot x^{(n)}_i $$

wherein $\gamma$ is a learning rate, and the numbers $\delta^{(n)}_j$ can be recursively calculated as $$ \delta^{(n)}_j = \left(\sum_k \delta^{(n+1)}_k \cdot w^{(n+1)}_{j,k}\right) \cdot f'\left(\sum_i x^{(n)}_i \cdot w^{(n)}_{i,j}\right) $$

based on $\delta^{(n+1)}_j$, if the (n+1)-th layer is not the output layer, and $$ \delta^{(n)}_j = \left(x^{(n+1)}_j - t^{(n+1)}_j\right) \cdot f'\left(x^{(n)}_i \cdot w^{(n)}_{i,j}\right) $$

if the (n+1)-th layer is the output layer 513, wherein f' is the first derivative of the activation function, and $t^{(n+1)}_j$ is the comparison training value for the j-th node of the output layer 513.

A convolutional neural network is a neural network that uses a convolution operation instead general matrix multiplication in at least one of its layers (so-called "convolutional layer"). In particular, a convolutional layer performs a dot product of one or more convolution kernels with the convolutional layer's input data/image, wherein the entries of the one or more convolution kernel are the parameters or weights that are adapted by training. In particular, one can use the Frobenius inner product and the ReLU activation function. A convolutional neural network can comprise additional layers, e.g., pooling layers, fully connected layers, and normalization layers.

By using convolutional neural networks input images can be processed in a very efficient way, because a convolution operation based on different kernels can extract various image features, so that by adapting the weights of the convolution kernel the relevant image features can be found during training. Furthermore, based on the weight-sharing in the convolutional kernels less parameters need to be trained, which prevents overfitting in the training phase and allows to have faster training or more layers in the network, improving the performance of the network.

Figure 6:
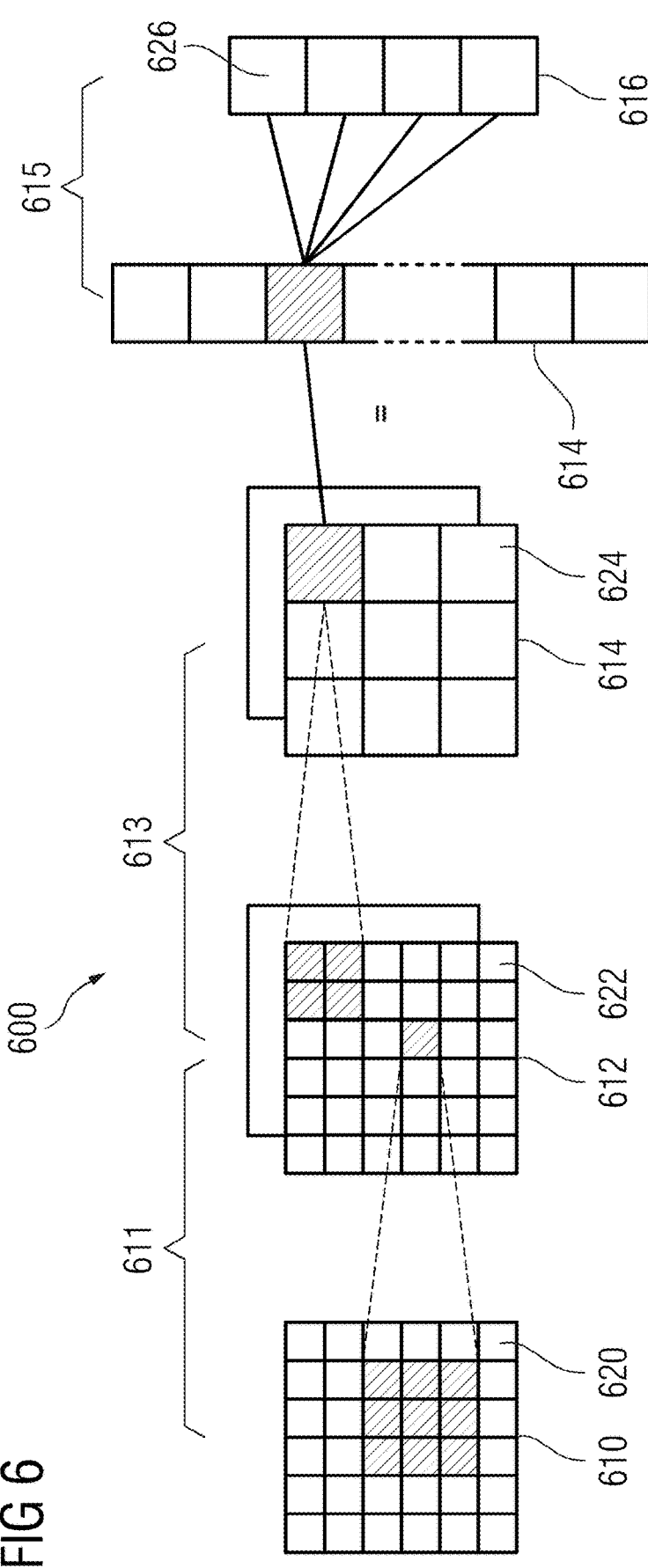
FIG. 6 shows a convolutional neural network that may be used to implement one or more embodiments.

FIG. 6 shows an embodiment of a convolutional neural network 600 that may be used to implement one or more machine learning models described herein. In the displayed embodiment, the convolutional neural network comprises 600 an input node layer 610, a convolutional layer 611, a pooling layer 613, a fully connected layer 614 and an output node layer 616, as well as hidden node layers 612, 614. Alternatively, the convolutional neural network 600 can comprise several convolutional layers 611, several pooling layers 613 and several fully connected layers 615, as well as other types of layers. The order of the layers can be chosen arbitrarily, usually fully connected layers 615 are used as the last layers before the output layer 616.

In particular, within a convolutional neural network 600 nodes 620, 622, 624 of a node layer 610, 612, 614 can be considered to be arranged as a d-dimensional matrix or as a d-dimensional image. In particular, in the two-dimensional case the value of the node 620, 622, 624 indexed with i and j in the n-th node layer 610, 612, 614 can be denoted as x(n)[i, j]. However, the arrangement of the nodes 620, 622, 624 of one node layer 610, 612, 614 does not have an effect on the calculations executed within the convolutional neural network 600 as such, since these are given solely by the structure and the weights of the edges.

A convolutional layer 611 is a connection layer between an anterior node layer 610 (with node values x(n−1)) and a posterior node layer 612 (with node values x(n)). In particular, a convolutional layer 611 is characterized by the structure and the weights of the incoming edges forming a convolution operation based on a certain number of kernels. In particular, the structure and the weights of the edges of the convolutional layer 611 are chosen such that the values x(n) of the nodes 622 of the posterior node layer 612 are calculated as a convolution x(n)=K*x(n−1) based on the values x(n−1) of the nodes 620 anterior node layer 610, where the convolution * is defined in the two-dimensional case as $$x_k^{(n)}[i, j] = \left(K * x^{(n-1)}\right)[i, j] = \sum_{i'} \sum_{j'} K\left[i^1, j^1\right] \cdot x^{(n-1)}\left[i - i^1, j - j^1\right].$$

Here the kernel K is a d-dimensional matrix (in this embodiment, a two-dimensional matrix), which is usually small compared to the number of nodes 620, 622 (e.g., a 3×3 matrix, or a 5×5 matrix). In particular, this implies that the weights of the edges in the convolution layer 611 are not independent, but chosen such that they produce said convolution equation. In particular, for a kernel being a 3×3 matrix, there are only 9 independent weights (each entry of the kernel matrix corresponding to one independent weight), irrespectively of the number of nodes 620, 622 in the anterior node layer 610 and the posterior node layer 612.

In general, convolutional neural networks 600 use node layers 610, 612, 614 with a plurality of channels, in particular, due to the use of a plurality of kernels in convolutional layers 611. In those cases, the node layers can be considered as (d+1)-dimensional matrices (the first dimension indexing the channels). The action of a convolutional layer 611 is then a two-dimensional example defined as $$x_k^{(n)}[i, j] =$$
$$\sum_a K_{a,b} * x^{(n-1)a}[i, j] = \sum_a \sum_{i'} \sum_{j'} K_{a,b}[i', j'] \cdot x^{(n-1)a}[i - i', j - j']$$

where $x^{(n-1)a}$ corresponds to the a-th channel of the anterior node layer 610, $x^{(n)b}$ corresponds to the b-th channel of the posterior node layer 612 and $K_{a,b}$ corresponds to one of the kernels. If a convolutional layer 611 acts on an anterior node layer 610 with A channels and outputs a posterior node layer 612 with B channels, there are A·B independent d-dimensional kernels $K_{a,b}$.

In general, in convolutional neural networks 600 activation functions are used. In this embodiment re ReLU (acronym for "Rectified Linear Units") is used, with R(z)=max(0, z), so that the action of the convolutional layer 611 in the two-dimensional example is $$x^{(n)b}[i, j] = R\left(\sum_a \left(K_{a,b} * x^{(n-1)a}\right)[i, j]\right) =$$
$$R\left(\sum_a \sum_{i'} \sum_{j'} K_{a,b}[i', j'] \cdot x^{(n-1)a}[i - i', j - j']\right)$$

It is also possible to use other activation functions, e.g., ELU (acronym for "Exponential Linear Unit"), LeakyReLU, Sigmoid, Tanh or Softmax.

In the displayed embodiment, the input layer 610 comprises 36 nodes 620, arranged as a two-dimensional 6×6 matrix. The first hidden node layer 612 comprises 72 nodes 622, arranged as two two-dimensional 6×6 matrices, each of the two matrices being the result of a convolution of the values of the input layer with a 3×3 kernel within the convolutional layer 611. Equivalently, the nodes 622 of the first hidden node layer 612 can be interpreted as arranged as a three-dimensional 2×6×6 matrix, wherein the first dimension correspond to the channel dimension.

The advantage of using convolutional layers 611 is that spatially local correlation of the input data can exploited by enforcing a local connectivity pattern between nodes of adjacent layers, in particular by each node being connected to only a small region of the nodes of the preceding layer.

A pooling layer 613 is a connection layer between an anterior node layer 612 (with node values x(n−1)) and a posterior node layer 614 (with node values x(n)). In particular, a pooling layer 613 can be characterized by the structure and the weights of the edges and the activation function forming a pooling operation based on a non-linear pooling function f. For example, in the two-dimensional case the values x(n) of the nodes 624 of the posterior node layer 614 can be calculated based on the values x(n−1) of the nodes 622 of the anterior node layer 612 as $$x^{(n)b}[i, j] = f\left(x^{(n-1)}[id_1, jd_2], \dots, x^{(n-1)b}[(i+1)d_1 - 1, (j+1)d_2 - 1]\right)$$

In other words, by using a pooling layer 613 the number of nodes 622, 624 can be reduced, by re-placing a number d1·d2 of neighboring nodes 622 in the anterior node layer 612 with a single node 622 in the posterior node layer 614 being calculated as a function of the values of said number of neighboring nodes. In particular, the pooling function f can be the max-function, the average or the L2-Norm. In particular, for a pooling layer 613 the weights of the incoming edges are fixed and are not modified by training.

The advantage of using a pooling layer 613 is that the number of nodes 622, 624 and the number of parameters is reduced. This leads to the amount of computation in the network being reduced and to a control of overfitting.

In the displayed embodiment, the pooling layer 613 is a max-pooling layer, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

In general, the last layers of a convolutional neural network 600 are fully connected layers 615. A fully connected layer 615 is a connection layer between an anterior node layer 614 and a posterior node layer 616. A fully connected layer 613 can be characterized by the fact that a majority, in particular, all edges between nodes 614 of the anterior node layer 614 and the nodes 616 of the posterior node layer are present, and wherein the weight of each of these edges can be adjusted individually.

In this embodiment, the nodes 624 of the anterior node layer 614 of the fully connected layer 615 are displayed both as two-dimensional matrices, and additionally as non-related nodes (indicated as a line of nodes, wherein the number of nodes was reduced for a better presentability). This operation is also denoted as "flattening". In this embodiment, the number of nodes 626 in the posterior node layer 616 of the fully connected layer 615 smaller than the number of nodes 624 in the anterior node layer 614. Alternatively, the number of nodes 626 can be equal or larger.

Furthermore, in this embodiment the Softmax activation function is used within the fully connected layer 615. By applying the Softmax function, the sum the values of all nodes 626 of the output layer 616 is 1, and all values of all nodes 626 of the output layer 616 are real numbers between 0 and 1. In particular, if using the convolutional neural network 600 for categorizing input data, the values of the output layer 616 can be interpreted as the probability of the input data falling into one of the different categories.

In particular, convolutional neural networks 600 can be trained based on the backpropagation algorithm. For preventing overfitting, methods of regularization can be used, e.g., dropout of nodes 620, . . . , 624, stochastic pooling, use of artificial data, weight decay based on the L1 or the L2 norm, or max norm constraints.

According to an aspect, the machine learning model may comprise one or more residual networks (ResNet). In particular, a ResNet is an artificial neural network comprising at least one jump or skip connection used to jump over at least one layer of the artificial neural network. In particular, a ResNet may be a convolutional neural network comprising one or more skip connections respectively skipping one or more convolutional layers. According to some examples, the ResNets may be represented as m-layer ResNets, where m is the number of layers in the corresponding architecture and, according to some examples, may take values of 34, 50, 101, or 152. According to some examples, such an m-layer ResNet may respectively comprise (m–2)/2 skip connections.

A skip connection may be seen as a bypass which directly feeds the output of one preceding layer over one or more bypassed layers to a layer succeeding the one or more bypassed layers. Instead of having to directly fit a desired mapping, the bypassed layers would then have to fit a residual mapping "balancing" the directly fed output.

Fitting the residual mapping is computationally easier to optimize than the directed mapping. What is more, this alleviates the problem of vanishing/exploding gradients during optimization upon training the machine learning models: if a bypassed layer runs into such problems, its contribution may be skipped by regularization of the directly fed output. Using ResNets thus brings about the advantage that much deeper networks may be trained.

In particular, a recurrent machine learning model is a machine learning model whose output does not only depend on the input value and the parameters of the machine learning model adapted by the training process, but also on a hidden state vector, wherein the hidden state vector is based on previous inputs used on for the recurrent machine learning model. In particular, the recurrent machine learning model can comprise additional storage states or additional structures that incorporate time delays or comprise feedback loops.

In particular, the underlying structure of a recurrent machine learning model can be a neural network, which can be denoted as recurrent neural network. Such a recurrent neural network can be described as an artificial neural network where connections between nodes form a directed graph along a temporal sequence. In particular, a recurrent neural network can be interpreted as directed acyclic graph. In particular, the recurrent neural network can be a finite impulse recurrent neural network or an infinite impulse recurrent neural network (wherein a finite impulse network can be unrolled and replaced with a strictly feedforward neural network, and an infinite impulse network cannot be unrolled and replaced with a strictly feedforward neural network).

In particular, training a recurrent neural network can be based on the BPTT algorithm (acronym for "backpropagation through time"), on the RTRL algorithm (acronym for "real-time recurrent learning") and/or on genetic algorithms.

By using a recurrent machine learning model input data comprising sequences of variable length can be used. In particular, this implies that the method cannot be used only for a fixed number of input datasets (and needs to be trained differently for every other number of input datasets used as input), but can be used for an arbitrary number of input datasets. This implies that the whole set of training data, independent of the number of input datasets contained in different sequences, can be used within the training, and that training data is not reduced to training data corresponding to a certain number of successive input datasets.

Figure 7:
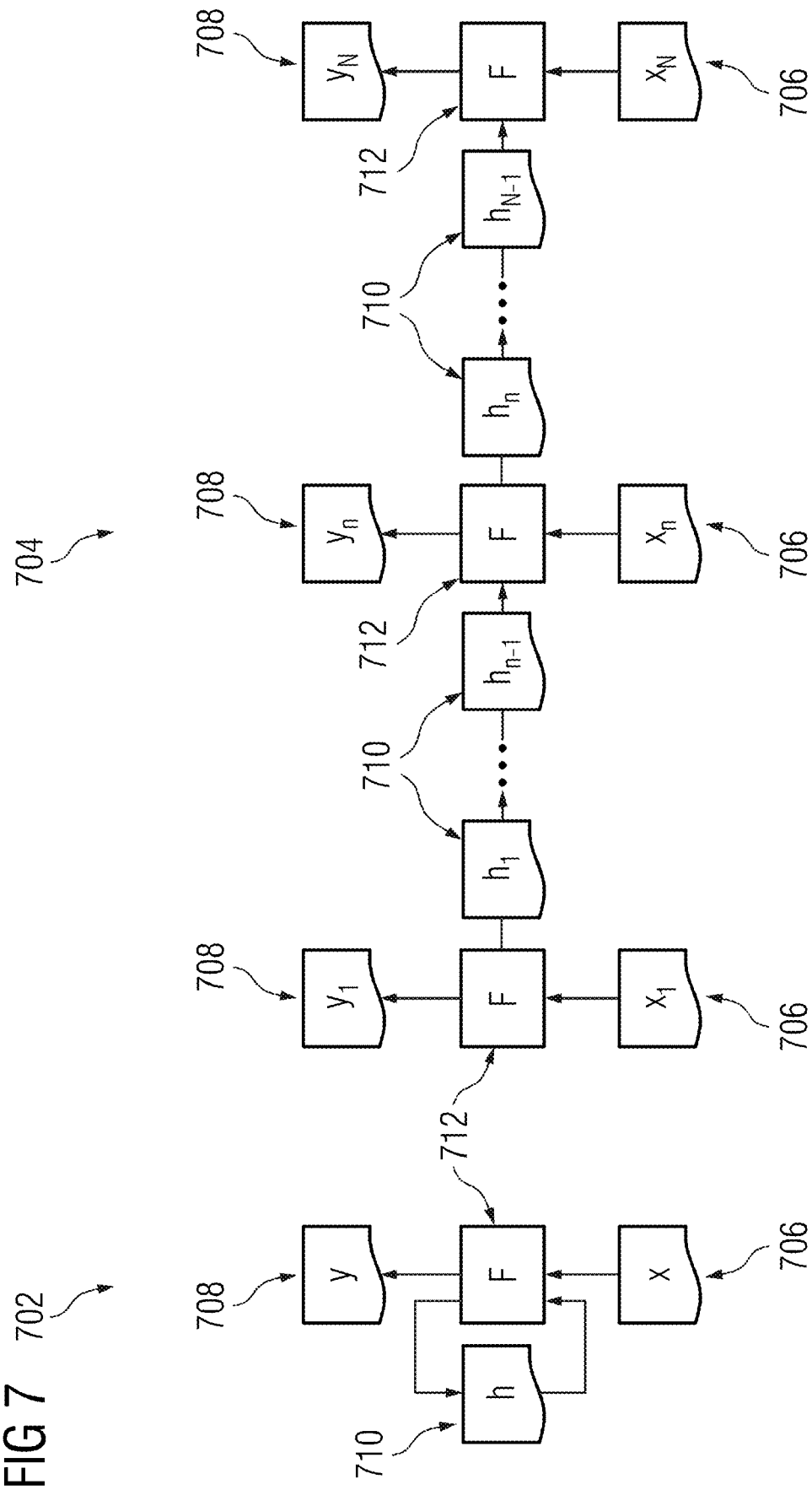
FIG. 7 shows a schematic structure of a recurrent machine learning model that may be used to implement one or more embodiments.

FIG. 7 shows the schematic structure of a recurrent machine learning model F, both in a recurrent representation 702 and in an unfolded representation 704, that may be used to implement one or more machine learning models described herein. The recurrent machine learning model takes as input several input datasets x, $x_1$, . . . , $x_N$ 706 and creates a corresponding set of output datasets y, $y_1$, . . . , $y_N$ 708. Furthermore, the output depends on a so-called hidden vector h, $h_1$, . . . , $h_N$ 710, which implicitly comprises information about input datasets previously used as input for the recurrent machine learning model F 712. By using these hidden vectors h, $h_1$, . . . , $h_N$ 710, a sequentiality of the input datasets can be leveraged.

In a single step of the processing, the recurrent machine learning model F 712 takes as input the hidden vector $h_{n-1}$ created within the previous step and an input dataset $x_n$. Within this step, the recurrent machine learning model F generates as output an updated hidden vector $h_n$ and an output dataset $y_n$. In other words, one step of processing calculates $(y_n, h_n)=F(x_n, h_{n-1})$, or by splitting the recurrent machine learning model F 712 into a part F(y) calculating the output data and F(h) calculating the hidden vector, one step of processing calculates $y_n=F^{(y)}(x_n, h_{n-1})$ and $h_n=F^{(h)}(x_n, h_{n-1})$. For the first processing step, $h_0$ can be chosen randomly or filled with all entries being zero. The parameters of the recurrent machine learning model F 712 that were trained based on training datasets before do not change between the different processing steps.

In particular, the output data and the hidden vector of a processing step depend on all the previous input datasets used in the previous steps. $y_n=F^{(y)}(x_n, F^{(h)}(x_{n-1}, h_{n-2}))$ and $h_n=F(h)(x_n, F^{(h)}(x_{n-1}, h_{n-2}))$.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatuses, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatuses, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-4. Certain steps or functions of the methods and workflows described herein, including one or more of the steps or functions of FIGS. 1-4, may be performed by a server or by another processor in a network-based cloud-computing system. Certain steps or functions of the methods and workflows described herein, including one or more of the steps of FIGS. 1-4, may be performed by a client computer in a network-based cloud computing system. The steps or functions of the methods and workflows described herein, including one or more of the steps of FIGS. 1-4, may be performed by a server and/or by a client computer in a network-based cloud computing system, in any combination.

Systems, apparatuses, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

A high-level block diagram of an example computer 802 that may be used to implement systems, apparatuses, and methods described herein is depicted in FIG. 8. Computer 802 includes a processor 804 operatively coupled to a data storage device 812 and a memory 810. Processor 804 controls the overall operation of computer 802 by executing computer program instructions that define such operations. The computer program instructions may be stored in data storage device 812, or other computer readable medium, and loaded into memory 810 when execution of the computer program instructions is desired. Thus, the method and workflow steps or functions of FIGS. 1-4 can be defined by the computer program instructions stored in memory 810 and/or data storage device 812 and controlled by processor 804 executing the computer program instructions. For example, the computer program instructions can be implemented as computer executable code programmed by one skilled in the art to perform the method and workflow steps or functions of FIGS. 1-4. Accordingly, by executing the computer program instructions, the processor 804 executes the method and workflow steps or functions of FIGS. 1-4. Computer 802 may also include one or more network interfaces 806 for communicating with other devices via a network. Computer 802 may also include one or more input/output devices 808 that enable user interaction with computer 802 (e.g., display, keyboard, mouse, microphone, speakers, buttons, etc.).

Processor 804 may include both general and special purpose microprocessors, and may be the sole processor or one of multiple processors of computer 802. Processor 804 may include one or more central processing units (CPUs), for example. Processor 804, data storage device 812, and/or memory 810 may include, be supplemented by, or incorporated in, one or more application-specific integrated circuits (ASICs) and/or one or more field programmable gate arrays (FPGAs).

Data storage device 812 and memory 810 each include a tangible non-transitory computer readable storage medium. Data storage device 812, and memory 810, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 808 may include peripherals, such as a printer, scanner, display screen, etc. For example, input/output devices 808 may include a display device such as a cathode ray tube (CRT) or liquid crystal display (LCD) monitor for displaying information to the user, a keyboard, and a pointing device such as a mouse or a trackball by which the user can provide input to computer 802.

An image acquisition device 814 can be connected to the computer 802 to input image data (e.g., medical images) to the computer 802. It is possible to implement the image acquisition device 814 and the computer 802 as one device. It is also possible that the image acquisition device 814 and the computer 802 communicate wirelessly through a network. In a possible embodiment, the computer 802 can be located remotely with respect to the image acquisition device 814.

Any or all of the systems, apparatuses, and methods discussed herein may be implemented using one or more computers such as computer 802.

One skilled in the art will recognize that an implementation of an actual computer or computer system may have other structures and may contain other components as well, and that FIG. 8 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving user input comprising 1) a description of desired medical images and 2) viewing preferences for the desired medical images; determining one or more nodes of a clinical knowledge ontological database that match the description of the desired medical images, the one or more matching nodes associated with one or more medical images in the clinical knowledge ontological database; generating a display layout of the one or more medical images based on the viewing preferences; and outputting the display layout.

Illustrative embodiment 2. The computer-implemented method of Illustrative embodiment 1, wherein: receiving user input comprising 1) a description of desired medical images and 2) viewing preferences for the desired medical images comprises receiving the user input further comprising a temporal description of the desired medical images; and determining one or more nodes of a clinical knowledge ontological database that match the description of the desired medical images comprises determining the one or more nodes of the clinical knowledge ontological database that match the description of the desired medical images based on the temporal description of the desired medical images.

Illustrative embodiment 3. The computer-implemented method of any one of Illustrative embodiments 1-2, wherein determining one or more nodes of a clinical knowledge ontological database that match the description of the desired medical images comprises: parsing the user input into vectors; performing a vector search between the vector representing the description of the desired medical images and vectors representing nodes of the clinical knowledge ontological database to identify a list of ranked nodes; and identifying one or more highest ranking nodes that satisfy a ranking threshold as the one or more nodes.

Illustrative embodiment 4. The computer-implemented method of any one of Illustrative embodiments 1-3, further comprising generating the clinical knowledge ontological database by: receiving one or more medical images; extracting features from the one or more medical images using one or more machine learning models; associating the extracted features with corresponding nodes of the clinical knowledge ontological database; and outputting the clinical knowledge ontological database with the extracted features associated with the corresponding nodes.

Illustrative embodiment 5. The computer-implemented method of any one of Illustrative embodiments 1-4, wherein the description of desired medical images comprises a description of an anatomical object of interest to which to navigate within one or more medical images and wherein the one or more matching nodes associated with one or more medical images in the clinical knowledge ontological database comprises one or more matching nodes associated with coordinates of the anatomical object of interest in the one or more medical images.

Illustrative embodiment 6. The computer-implemented method of any one of Illustrative embodiments 1-5, wherein the description of the desired medical images is defined based on at least one of imaging modality, acquisition parameter, acquisition orientation, image appearance, anatomical field of view, or classifications and detections.

Illustrative embodiment 7. The computer-implemented method of any one of Illustrative embodiments 1-6, wherein the viewing preferences are defined based on at least one of anatomical display orientation, windowing, or rendering mode.

Illustrative embodiment 8. The computer-implemented method of any one of Illustrative embodiments 1-7, wherein generating a display layout of the one or more medical images based on the viewing preferences comprises: translating the viewing preferences to rendering parameters using a language model.

Illustrative embodiment 9. The computer-implemented method of any one of Illustrative embodiments 1-8, wherein outputting the display layout comprises: displaying the display layout on a display device.

Illustrative embodiment 10. An apparatus comprising: means for receiving user input comprising 1) a description of desired medical images and 2) viewing preferences for the desired medical images; means for determining one or more nodes of a clinical knowledge ontological database that match the description of the desired medical images, the one or more matching nodes associated with one or more medical images in the clinical knowledge ontological database; means for generating a display layout of the one or more medical images based on the viewing preferences; and means for outputting the display layout.

Illustrative embodiment 11. The apparatus of illustrative embodiment 10, wherein: the means for receiving user input comprising 1) a description of desired medical images and 2) viewing preferences for the desired medical images comprises means for receiving the user input further comprising a temporal description of the desired medical images; and the means for determining one or more nodes of a clinical knowledge ontological database that match the description of the desired medical images comprises means for determining the one or more nodes of the clinical knowledge ontological database that match the description of the desired medical images based on the temporal description of the desired medical images.

Illustrative embodiment 12. The apparatus of any one of Illustrative embodiments 10-11, wherein the means for determining one or more nodes of a clinical knowledge ontological database that match the description of the desired medical images comprises: means for parsing the user input into vectors; means for performing a vector search between the vector representing the description of the desired medical images and vectors representing nodes of the clinical knowledge ontological database to identify a list of ranked nodes; and means for identifying one or more highest ranking nodes that satisfy a ranking threshold as the one or more nodes.

Illustrative embodiment 13. The apparatus of any one of Illustrative embodiments 10-12, further comprising means for generating the clinical knowledge ontological database by: means for receiving one or more medical images; means for extracting features from the one or more medical images using one or more machine learning models; means for associating the extracted features with corresponding nodes of the clinical knowledge ontological database; and means for outputting the clinical knowledge ontological database with the extracted features associated with the corresponding nodes.

Illustrative embodiment 14. The apparatus of any one of Illustrative embodiments 10-13, wherein the description of desired medical images comprises a description of an anatomical object of interest to which to navigate within one or more medical images and wherein the one or more matching nodes associated with one or more medical images in the clinical knowledge ontological database comprises one or more matching nodes associated with coordinates of the anatomical object of interest in the one or more medical images.

Illustrative embodiment 15. A non-transitory computer-readable medium comprising instructions which, when executed by a computer, cause the computer to carry out operations comprising: receiving user input comprising 1) a description of desired medical images and 2) viewing preferences for the desired medical images; determining one or more nodes of a clinical knowledge ontological database that match the description of the desired medical images, the one or more matching nodes associated with one or more medical images in the clinical knowledge ontological database; generating a display layout of the one or more medical images based on the viewing preferences; and outputting the display layout.

Illustrative embodiment 16. The non-transitory computer-readable medium of illustrative embodiment 15, wherein: receiving user input comprising 1) a description of desired medical images and 2) viewing preferences for the desired medical images comprises receiving the user input further comprising a temporal description of the desired medical images; and determining one or more nodes of a clinical knowledge ontological database that match the description of the desired medical images comprises determining the one or more nodes of the clinical knowledge ontological database that match the description of the desired medical images based on the temporal description of the desired medical images.

Illustrative embodiment 17. The non-transitory computer-readable medium of any one of Illustrative embodiments 15-16, wherein the description of the desired medical images is defined based on at least one of imaging modality, acquisition parameter, acquisition orientation, image appearance, anatomical field of view, or classifications and detections.

Illustrative embodiment 18. The non-transitory computer-readable medium of any one of Illustrative embodiments 15-17, wherein the viewing preferences are defined based on at least one of anatomical display orientation, windowing, or rendering mode.

Illustrative embodiment 19. The non-transitory computer-readable medium of any one of Illustrative embodiments 15-18, wherein generating a display layout of the one or more medical images based on the viewing preferences comprises: translating the viewing preferences to rendering parameters using a language model.

Illustrative embodiment 20. The non-transitory computer-readable medium of any one of Illustrative embodiments 15-19, wherein outputting the display layout comprises: displaying the display layout on a display device.

The invention claimed is:

1. A computer-implemented method comprising:
receiving user input comprising 1) a description of desired medical images and 2) viewing preferences for the desired medical images;
determining one or more nodes of a graph of a clinical knowledge ontological database that match the description of the desired medical images, the graph comprising 1) a plurality of nodes each associated with clinical nomenclature of medical images and 2) edges connecting at least some of the plurality of nodes, wherein at least one of the plurality of nodes is associated with at least one medical image that corresponds to its associated clinical nomenclature, wherein the one or more nodes of the graph are determined by:
extracting a vector representation of the description of the desired medical images from the user input,
performing a vector search between the vector representation of the description of the desired medical images and a vector representation of each of the plurality of nodes of the graph of the clinical knowledge ontological database, and
identifying the one or more nodes as matching the description of the desired medical images based on results of the vector search;
generating a display layout of one or more medical images associated with the one or more nodes based on the viewing preferences; and
outputting the display layout.

2. The computer-implemented method of claim 1, wherein:
receiving user input comprising 1) a description of desired medical images and 2) viewing preferences for the desired medical images comprises receiving the user input further comprising a temporal description of the desired medical images; and
determining one or more nodes of a graph of a clinical knowledge ontological database that match the description of the desired medical images comprises determining the one or more nodes of the graph of the clinical knowledge ontological database that match the description of the desired medical images based on the temporal description of the desired medical images.

3. The computer-implemented method of claim 1, wherein identifying the one or more nodes as matching the description of the desired medical images based on results of the vector search comprises:
identifying one or more highest ranking nodes that satisfy a ranking threshold as the one or more nodes.

4. The computer-implemented method of claim 1, further comprising generating the clinical knowledge ontological database by:
extracting features from the at least one medical image using one or more machine learning models;
associating the extracted features with corresponding ones of the plurality of nodes of the graph of the clinical knowledge ontological database; and
outputting the clinical knowledge ontological database with the extracted features associated with the corresponding nodes.

5. The computer-implemented method of claim 1, wherein the description of desired medical images comprises a description of an anatomical object of interest to which to navigate within one or more medical images and wherein the one or more matching nodes associated with one or more medical images in the graph of the clinical knowledge ontological database comprises one or more matching nodes associated with coordinates of the anatomical object of interest in the one or more medical images.

6. The computer-implemented method of claim 1, wherein the description of the desired medical images is defined based on at least one of imaging modality, acquisition parameter, acquisition orientation, image appearance, anatomical field of view, or classifications and detections.

7. The computer-implemented method of claim 1, wherein the viewing preferences are defined based on at least one of anatomical display orientation, windowing, or rendering mode.

8. The computer-implemented method of claim 1, wherein generating a display layout of the one or more medical images based on the viewing preferences comprises:

translating the viewing preferences to rendering parameters using a language model.

9. The computer-implemented method of claim 1, wherein outputting the display layout comprises:

displaying the display layout on a display device.

10. An apparatus comprising:

means for receiving user input comprising 1) a description of desired medical images and 2) viewing preferences for the desired medical images;

means for determining one or more nodes of a graph of a clinical knowledge ontological database that match the description of the desired medical images, the graph comprising 1) a plurality of nodes each associated with clinical nomenclature of medical images and 2) edges connecting at least some of the plurality of nodes, wherein at least one of the plurality of nodes is associated with at least one medical image that corresponds to its associated clinical nomenclature, wherein the one or more nodes of the graph are determined by extracting a vector representation of the description of the desired medical images from the user input, performing a vector search between the vector representation of the description of the desired medical images and a vector representation of each of the plurality of nodes of the graph of the clinical knowledge ontological database, and identifying the one or more nodes as matching the description of the desired medical images based on results of the vector search;

means for generating a display layout of one or more medical images associated with the one or more nodes based on the viewing preferences; and means for outputting the display layout.

11. The apparatus of claim 10, wherein:

the means for receiving user input comprising 1) a description of desired medical images and 2) viewing preferences for the desired medical images comprises means for receiving the user input further comprising a temporal description of the desired medical images; and the means for determining one or more nodes of a graph of a clinical knowledge ontological database that match the description of the desired medical images comprises determining the one or more nodes of the graph of the clinical knowledge ontological database that match the description of the desired medical images based on the temporal description of the desired medical images.

12. The apparatus of claim 10, wherein the means for identifying the one or more nodes as matching the description of the desired medical images based on results of the vector search comprises:

means for identifying one or more highest ranking nodes that satisfy a ranking threshold as the one or more nodes.

13. The apparatus of claim 10, further comprising means for generating the clinical knowledge ontological database by:

means for extracting features from the at least one medical image using one or more machine learning models;

means for associating the extracted features with corresponding ones of the plurality of nodes of the graph of the clinical knowledge ontological database; and means for outputting the clinical knowledge ontological database with the extracted features associated with the corresponding nodes.

14. The apparatus of claim 10, wherein the description of desired medical images comprises a description of an anatomical object of interest to which to navigate within one or more medical images and wherein the one or more matching nodes associated with one or more medical images in the graph of the clinical knowledge ontological database comprises one or more matching nodes associated with coordinates of the anatomical object of interest in the one or more medical images.

15. A non-transitory computer-readable medium comprising instructions which, when executed by a computer, cause the computer to carry out operations comprising:

receiving user input comprising 1) a description of desired medical images and 2) viewing preferences for the desired medical images;

determining one or more nodes of a graph of a clinical knowledge ontological database that match the description of the desired medical images, the graph comprising 1) a plurality of nodes each associated with clinical nomenclature of medical images and 2) edges connecting at least some of the plurality of nodes, wherein at least one of the plurality of nodes is associated with at least one medical image that corresponds to its associated clinical nomenclature, wherein the one or more nodes of the graph are determined by:

extracting a vector representation of the description of the desired medical images from the user input, performing a vector search between the vector representation of the description of the desired medical images and a vector representation of each of the plurality of nodes of the graph of the clinical knowledge ontological database, and identifying the one or more nodes as matching the description of the desired medical images based on results of the vector search;

generating a display layout of one or more medical images associated with the one or more nodes based on the viewing preferences; and outputting the display layout.

16. The non-transitory computer-readable medium of claim 15, wherein:

receiving user input comprising 1) a description of desired medical images and 2) viewing preferences for the desired medical images comprises receiving the user input further comprising a temporal description of the desired medical images; and determining one or more nodes of a graph of a clinical knowledge ontological database that match the description of the desired medical images comprises determining the one or more nodes of the graph of the clinical knowledge ontological database that match the description of the desired medical images based on the temporal description of the desired medical images.

17. The non-transitory computer-readable medium of claim 15, wherein the description of the desired medical images is defined based on at least one of imaging modality, acquisition parameter, acquisition orientation, image appearance, anatomical field of view, or classifications and detections.

18. The non-transitory computer-readable medium of claim 15, wherein the viewing preferences are defined based on at least one of anatomical display orientation, windowing, or rendering mode.

19. The non-transitory computer-readable medium of claim 15, wherein generating a display layout of the one or more medical images based on the viewing preferences comprises:

translating the viewing preferences to rendering parameters using a language model.

20. The non-transitory computer-readable medium of claim 15, wherein outputting the display layout comprises:

displaying the display layout on a display device.

\* \* \* \* \*